United States Patent [19]
Kiri et al.

[11] Patent Number: 5,151,588
[45] Date of Patent: Sep. 29, 1992

[54] RADIATION IMAGING APPARATUS HAVING DETECTION ELEMENTS OF VARYING SIZES

[75] Inventors: Motosada Kiri, Kyoto; Susumu Adachi, Osaka, both of Japan

[73] Assignee: Shimadzu Corporation, Kyoto, Japan

[21] Appl. No.: 807,632

[22] Filed: Dec. 13, 1991

Related U.S. Application Data

[63] Continuation of Ser. No. 612,958, Nov. 15, 1990, abandoned.

[30] Foreign Application Priority Data

Nov. 24, 1989 [JP] Japan ................... 1-305646

[51] Int. Cl.⁵ ............................................. H01J 40/14
[52] U.S. Cl. .............................. 250/208.1; 358/213.15
[58] Field of Search ............... 250/208.1; 358/213.15, 358/213.22, 213.27; 357/30 D

[56] References Cited

U.S. PATENT DOCUMENTS

| | | | |
|---|---|---|---|
| 4,383,327 | 5/1983 | Kruger | 378/19 |
| 4,641,359 | 2/1987 | Okibayashi et al. | 250/208.1 |
| 4,889,984 | 12/1989 | Sedgbeer | 250/208.1 |

FOREIGN PATENT DOCUMENTS

| | | |
|---|---|---|
| 0137487 | 4/1985 | European Pat. Off. |
| 0217456 | 4/1987 | European Pat. Off. |
| 0287197 | 10/1988 | European Pat. Off. |
| 0362427 | 4/1990 | European Pat. Off. |
| 2613831 | 10/1988 | France |

Primary Examiner—David C. Nelms
Assistant Examiner—K. Shami
Attorney, Agent, or Firm—Wegner, Cantor, Mueller & Player

[57] ABSTRACT

A radiation imaging apparatus provided with a detector array comprising a plurality of detector units, each of which, in turn, comprises a plurality of X-ray detecting elements each having a photosensitive surface of a different area from those of the other elements and corresponds to one picture element or pixel of a display, the output signal from one or more of the X-ray detecting elements of each of the detector units being used as image information for a corresponding one of the pixels of the display. While the X-ray dose remains at a low level, the detection output from the detecting element having a large photosensitive surface or the sum of the output from that element and the outputs from the other elements having smaller photosensitive surfaces is used as pixel information to form an image of the object being examined. When the radiation dose increases to a predetermined high level, the result of detection by only the element having a small photosensitive surface is used as pixel information.

3 Claims, 2 Drawing Sheets

RADIATION IMAGING APPARATUS HAVING DETECTION ELEMENTS OF VARYING SIZES

This application is a continuation of U.S. application Ser. No. 07/612,958, filed Nov. 15, 1990, now abandoned.

BACKGROUND OF THE INVENTION

This invention relates to an apparatus for producing an X-ray image by using an array of X-ray detecting elements, such as an X-ray computed tomograph commonly referred to as an X-ray CT for medical use or non-destructive testing apparatus for industrial use.

The X-ray imaging apparatus is provided with a detector array composed of a plurality of X-ray detecting elements for detecting X-rays from an object being examined. For collection of data to obtain an X-ray image of the object, it has been customary to conduct an analog conversion of the current output from each of the radiation detecting elements to corresponding voltage signals. In recent years, what is called the photon counting system has been proposed, in which the pulse-like signals produced by each of the X-ray detecting elements are counted to obtain necessary image information.

The analog current-voltage conversion system has a disadvantage that the dynamic range of the system is so low that satisfactory images cannot be obtained. In particular, as the level of the output signal from the detecting elements lowers, the signal to noise ratio decreases because of remaining constant amplifier noise, so that there is a limit to detection of the signal.

The photon counting system has no such limit in a low range of radiation dose. As the radiation dose increases, however, the X-ray photons from the object under examination are more likely to be miscounted, so that there is a limit to detection of the radiation at a higher level of radiation dose.

After all, neither of the two systems is able to provide a sufficient performance to produce quality images.

Accordingly, the primary object of the invention is to eliminate the above disadvantages of the prior art systems and to provide an X-ray imaging apparatus which has a wider dynamic range than the prior art systems.

The invention will be described in detail with reference to the accompanying drawings.

SUMMARY OF THE INVENTION

In the X-ray imaging apparatus of the invention, the output signals from a detector array is applied to a signal processing circuit of the photon counting type so as to determine the X-ray radiation dose, and the result of the determination is used as pixel information to form an X-ray image of the object being examined. The detector array comprises a plurality of detector units, each of which, in turn, comprises a plurality of X-ray detecting elements each having a photosensitive surface of a different area from those of the other elements. Each of the detector units corresponds to one picture element or pixel of a display unit, and the output signal from one or more of the X-ray detecting elements of each of the detector units is used as image information for a corresponding one of the pixels of the display.

The X-rays from an object being examined enter the detecting elements of each of the detector units. The detecting element having a large photosensitive surface receives a higher radiation dose than the detecting elements having smaller photosensitive surface areas. As the radiation dose increases, errors are likely to occur to the result of detection by the detecting element having a large photosensitive surface due to miscounting. With the detecting elements having smaller photosensitive surfaces, however, accurate detection is ensured up to a higher level of radiation dose.

In accordance with the invention, while the X-ray dose remains at a low level, the detection output from the detecting element having a large photosensitive surface or the sum of the output from that element and the outputs from the other elements having smaller photosensitive surfaces is used as pixel information to form an image of the object being observed. When the dose increases to a predetermined high level, the result of detection by only the element having a small photosensitive surface is used as pixel information, thereby to extend the limit of detection to a higher level of radiation dose than in the photon counting system.

The invention will be described in detail with reference to the accompanying drawings.

DESCRIPTION OF PREFERRED EMBODIMENTS

Figure 1:
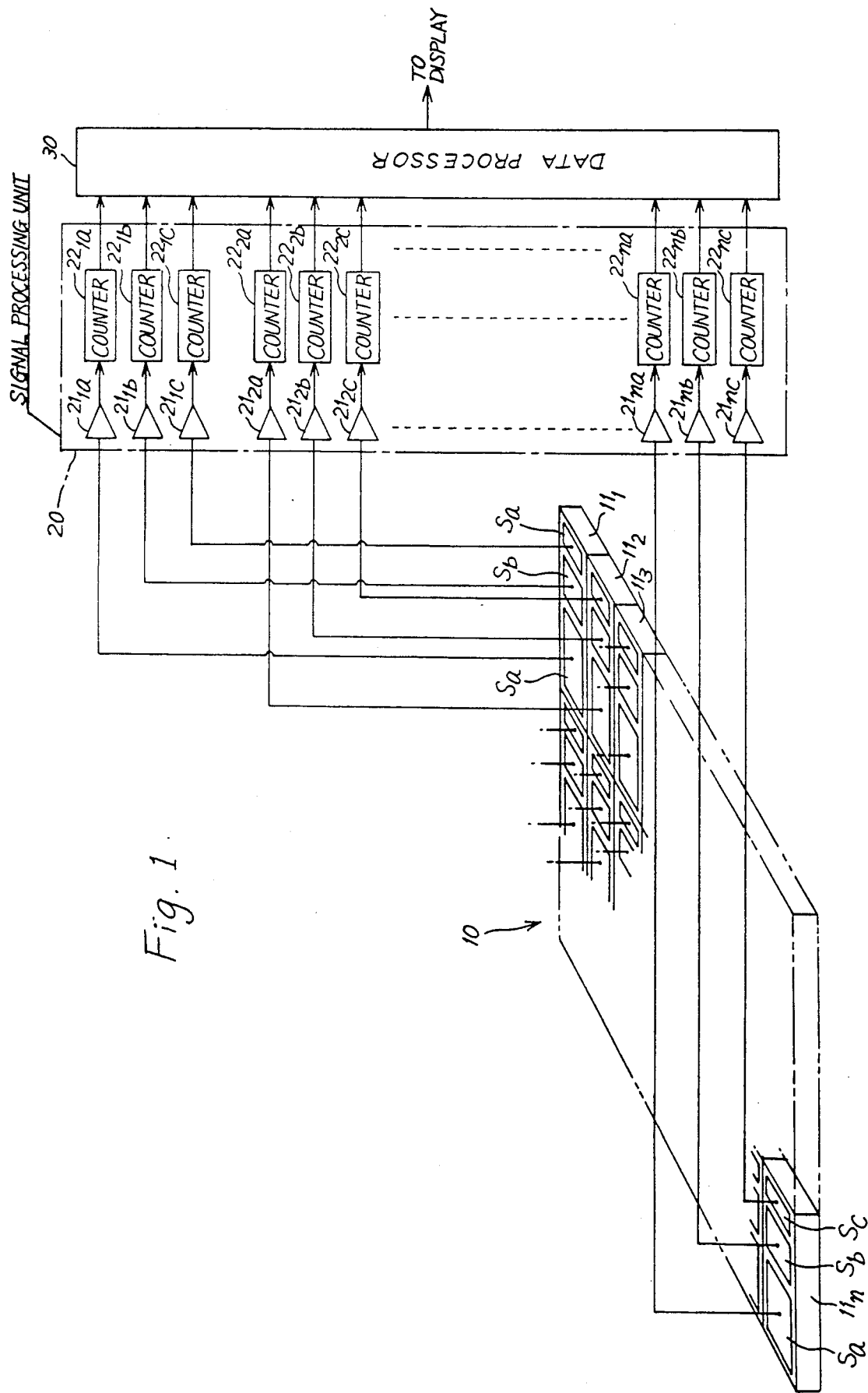
FIG. 1 is a schematic diagram of one embodiment of the invention.

FIG. 1 shows one embodiment of the invention, wherein there is shown a detector array 10 which comprises a plurality of detector units $11_1$, $11_2$, ... $11_n$ arranged two-dimensionally, that is, on a plane. Each of the detector units $11_1$, ... $11_n$ comprises a plurality, say, three detecting elements Sa, Sb and Sc each having a photosensitive surface of a different area from those of the other elements.

The output signals from the detecting elements Sa, Sb and Sc of each of the detector units $11_1$, ... $11_n$ are applied to a signal processing unit 20 of a photon counting type. In particular, the unit 20 comprises a plurality of amplifiers such as charge sensitive amplifiers $21_{1a}$, $21_{1b}$, $21_{1c}$, $21_{2a}$, $21_{2b}$, $21_{2c}$, ... $21_{na}$, $21_{nb}$, $21_{nc}$, and a plurality of corresponding counters $22_{1a}$, $22_{1b}$, $22_{1c}$, $22_{2a}$, $21_{2b}$, $22_{2c}$, ... $22_{na}$, $22_{nb}$, $22_{nc}$ connected to the outputs of the amplifiers $21_{1a}$, ... $21_{nc}$, respectively. The output from each of the detecting elements Sa, Sb and Sc of each of the detector units $11_1$, ... $11_n$ is amplified by the corresponding one of the amplifiers $21_{1a}$, ... $21_{nc}$ to a logic level so as to become a pulse-like voltage signal, which is applied to the corresponding one of the counters $22_{1a}$, ... $21_{nc}$. In this manner, the numbers of X-ray photons incident on the detecting elements are counted by the respective counters.

The outputs from the counters are applied to a data processor 30, which provides necessary data for forming an X-ray image of the object under examination. The data processor 30 is so designed that, with each of the detector units $11_1$, ... $11_n$ corresponding to one of the pixels of a display unit on which the image of an object under examination is to be displayed, the processor operates in accordance with an algorithm to be described hereinafter to automatically determine which of the detecting elements Sa, Sb and Sc of each of the detector units is to be selected to obtain pixel information from its output, and to form an image in accordance with the pixel information obtained from the selected detecting element.

Figure 2:
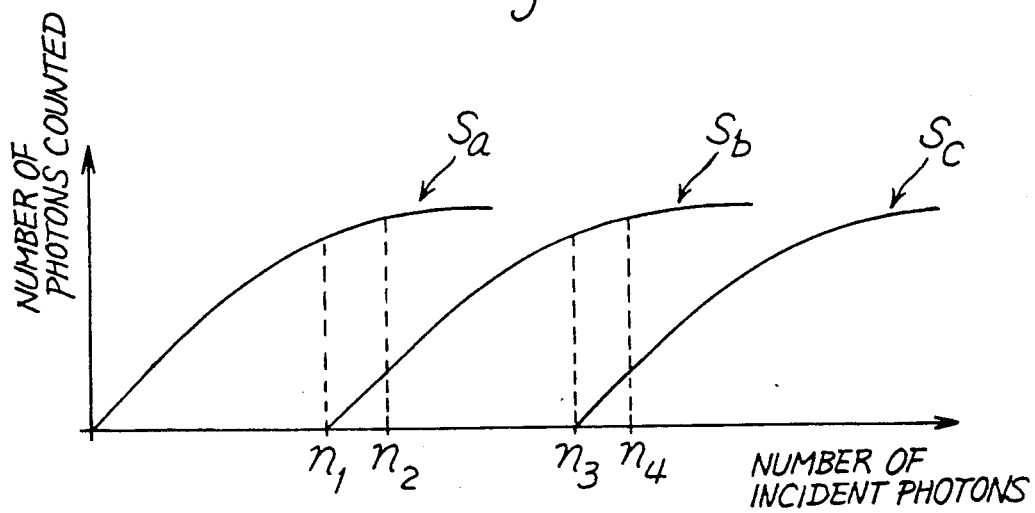
FIG. 2 is a graph showing the relation between the number of incident X-ray photons on the X-ray detecting elements provided in the apparatus of FIG. 1 and the number of X-ray photons actually counted.

As previously mentioned, with a given fixed amount of radiation incident on the detector array, as the area of a detecting element increases, the number of X-ray photons incident on the element increases so that miscounting of photons is more likely to occur. FIG. 2 shows a graph showing the relation between the number of photons incident on each of the detecting elements Sa, Sb and Sc having different photosensitive surface areas and the number of photons actually counted, with the number of photons counted taken along the ordinate and the number of photons incident on the detecting elements taken along the abscissa. The curves designated by Sa, Sb and Sc result from the corresponding detecting elements Sa, Sb and Sc.

As shown in the graph, the detecting element Sa having a large photosensitive surface detects photons with a high sensitivity in the range of low radiation dose, with the line Sa in the graph being linear in the low range. As the radiation dose increases, however, due to miscounting the linear relation between the number of X-ray photons that hit the detecting element having a large photosensitive surface and the number of X-ray photons that are actually counted comes to be lost. In other words, the latter number will not be proportional to the former number in a range of higher radiation dose.

On the other hand, although the detecting element Sb or Sc having a smaller photosensitive surface has a lower sensitivity than the detecting element Sa in the range of low radiation dose, the above-mentioned linearity is maintained in the range of higher radiation dose.

Therefore, if the number of counts of the photons from only the detecting element Sa having a large photosensitive surface, or the sum of the numbers of counts of the photons from the elements Sa and Sb, or Sa, Sb and Sc is used as image information for the pixel corresponding to the detector unit when the radiation dose incident thereon is in a low range, and the number of counts of the photons from the detecting element Sb or Sc is used when the radiation dose is in a high range, it is possible even with the photon counting system to provide an X-ray image with a high degree of accuracy in a range of high as well as low radiation dose.

Suppose that the relation between the number of the photons incident on each of the detecting elements and those of the photons actually counted is as shown in FIG. 2. While the number of incident photons is bellow $n_1$, the number of counts by the element Sa is used. When the number of incident photons is between $n_1$ and $n_2$, the sum of the numbers of counts by both the elements Sa and Sb is used. When the number of incident photons is between $n_3$ and $n_4$, the sum of the numbers of counts by both the elements Sb and Sc is used. Finally, when the number of incident photons exceeds $n_4$, the number of counts by the element Sc only is used. In this manner it is possible to form an accurate X-ray image from a low to a high level of radiation dose. In this case it is necessary to correct the counts by the detecting elements Sa, Sb and Sc in accordance with the areas of the photosensitive surfaces of the elements.

The previously mentioned algorithm used by the data processor 30 is such that it determines whether or not the number of photons counted by each of the counters $22_{1a}, \ldots 22_{nc}$ connected to the detecting elements Sa, Sb and Sc of the detector units $11_1, \ldots 11_n$ exceeds a preset value and, on the basis of the result of the determination, selects one or more of the detecting elements Sa, Sb and Sc the number of photons counted by which is to be used as pixel information for forming an image of an object under examination in the previously mentioned manner.

In accordance with the invention, the data processor 30 need not necessarily be provided with the above-mentioned function of automatically selecting the detecting elements. The arrangement may also be such that an operator selets one or more of the detecting elements when a measurement is conducted.

In the illustrated embodiment, each of the detector units which constitutes one pixel comprises three detecting elements Sa, Sb and Sc. They may also comprise two or more detecting elements. The detector array may comprise detecting elements having a photosensitive surface of any other suitable shape than in the illustrated embodiment.

Figure 3:
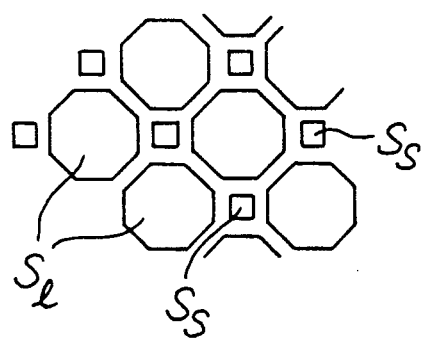
FIG. 3 shows the shapes of the detecting elements and a layout of the detector array composed of the elements in another embodiment of the invention.

FIG. 3 shows another embodiment of the invention, wherein the detector array comprises a plurality of large detecting elements S1 having a photosensitive surface of octagonal shape and a plurality of small detecting elements Ss having a photosensitive surface of square shape, with four large elements being arranged adjacent the four sides of one small square element.

The detecting elements constituting the detector array may be arranged linearly or two-dimensionally. The array may be held stationary or so arranged as to be able to be scanned.

As mentioned above, in the X-ray imaging apparatus of the invention each of the detecting elements constituting a detector unit has a photosensitive surface of a different area than the other elements, and one or more of the detecting elements is selected in accordance with the radiation dose they receive so that the number of counts of photons by the selected element or elements is used as pixel information to form an X-ray image of the object under examination. Basically, the apparatus is a photon counting system having an advantage that it is free of noise and can form an X-ray image with a high degree of accuracy even in a range of low radiation dose. At the same time, the disadvantage of the photon counting system that there is a limit to detection in a range of high radiation dose due to miscounting can be eliminated, so that it becomes possible to obtain accurate X-ray images in a very wide dynamic range from a low to a high level of radiation dose.

What we claim is:

1. A radiation imaging apparatus comprising:
   means for exposing an object to be examined to electromagnetic radiation;
   a detector array comprising a plurality of radiation detector units each of which corresponds to one of the pixels of a display and comprises a plurality of radiation detecting elements for detecting the radiation from said object under examination, each of said detecting elements having a photosensitive surface of a different area from those of the other detecting elements;
   a signal processing circuit of a photon counting type for processing the output signals of said detecting elements to produce an output corresponding to the number of the photons detected by each of said detecting elements; and a data processor for selecting one or more of said detecting elements of each of said detector units in accordance with the radiation dose received by said detecting elements so that the output of said selected one or more detecting elements is used as pixel information to form a radiation image of said object on said display.

2. The apparatus of claim 1, wherein said signal processing circuit comprises a plurality of amplifiers each connected to one of said detecting elements to produce an output pulse in accordance with the radiation dose received by said detecting elements, and a plurality of pulse counters each connected to one of said amplifiers to count said output pulses from each of said amplifiers so as to produce an output corresponding to the number of counts of said pulses.

3. The apparatus of claim 1, wherein said data processor operates in such a manner that while the radiation dose received by said detecting elements remains at a low level, either the output from that one of said detecting elements of each of said detector units which has a large photosensitive surface, or the sum of the output from said one detecting element and the outputs from said other detecting elements which have smaller photosensitive surfaces is used as pixel information to be supplied to said display to form a radiation image of said object, and that when said radiation dose increases to a predetermined high level, the output from that one of said detecting elements of each of said detector units which has a small photosensitive surface is used as pixel information to be supplied to said display to form a radiation image of said object.

* * * * *